United States Patent [19]

Tricerri et al.

[11] Patent Number: 4,508,719
[45] Date of Patent: Apr. 2, 1985

[54] HYDROXYIMINO AND ALKOXYIMINO DERIVATIVES OF 1,4-DIHYDROPYRIDINE AND ANTI-HYPERTENSIVE COMPOSITIONS

[75] Inventors: Silvia Z. Tricerri, Carimate; Cesare Casagrande, Arese; Franco De Marchi, Milan; Massimo Nicola, Pavia, all of Italy

[73] Assignee: Pierrel S.p.A., Napoli, Italy

[21] Appl. No.: 498,248

[22] Filed: May 26, 1983

[30] Foreign Application Priority Data

Jun. 3, 1982 [IT] Italy ................ 21679 A/82
May 11, 1983 [IT] Italy ................ 21044 A/83

[51] Int. Cl.³ ............... A61K 31/535; A61K 31/455; C07D 211/82; C07D 413/12
[52] U.S. Cl. .................... 514/236; 544/131; 544/333; 544/365; 544/405; 546/318; 546/194; 546/257; 546/283; 546/284; 546/280; 546/276; 514/252; 514/269; 514/318; 514/335; 514/340; 514/341; 514/342; 514/356
[58] Field of Search .............. 544/131, 365, 405, 333; 546/318, 284, 194, 280, 257, 276, 283; 424/266, 250, 251, 248.55

[56] References Cited

U.S. PATENT DOCUMENTS 4,339,584 7/1982 Gruett et al. .................. 424/266

OTHER PUBLICATIONS

Merck Index, Ninth Edition, (1976) p. ONR-80.

Primary Examiner—Henry R. Jiles
Assistant Examiner—Dale A. Bjorkman
Attorney, Agent, or Firm—Bucknam and Archer

[57] ABSTRACT

Compounds of formula I:

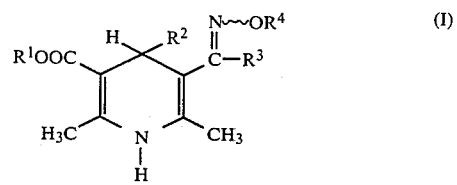

are described in which $R^1$ is a linear or branched alkyl radical containing between 1 and 5 carbon atoms, the alkyl radical being unsubstituted or substituted by an alkoxy group; $R^2$ is an unsubstituted phenyl of phenyl substituted by a nitro group; $R^3$ is hydrogen or a linear or branched alkyl residue containing between 1 and 4 carbon atoms, the alkyl radical being unsubstituted or substituted by at least one alkoxy or fluorine atom or both alkoxy and fluorine atoms; $R^4$ is hydrogen or a linear or branched alkyl containing between 1 and 4 carbon atoms, the alkyl radical being unsubstituted or substituted by alkoxy, carbalkoxy, dialkylamino, 1-aryl or 1-heteroarylpiperazinyl, aryl or a monocyclic 5 or 6 membered heterocycle in which at least one of the heteroatoms is N,O,S such as 1-piperidinyl, 4-morpholinyl or $R_4$ is alkenyl or cyclo$(C_3-C_6)$alkyl; and enantiomers, racemates, diastereoisomers and isomers (E) and (Z) and their salts with pharmaceutically acceptable acids.

The novel compounds exhibit calcium-antagonistic activity.

17 Claims, No Drawings

HYDROXYIMINO AND ALKOXYIMINO DERIVATIVES OF 1,4-DIHYDROPYRIDINE AND ANTI-HYPERTENSIVE COMPOSITIONS

The present invention relates to hydroxyimino and alkoxyimino derivatives of 1,4-dihydropyridine of general formula I

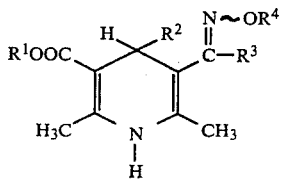

in which

- $R^1$ is a linear or branched alkyl radical of 1–5 carbon atoms and in which one atom of hydrogen may also be substituted by an alkoxy group;
- $R^2$ is a phenyl group which may also be substituted by a nitro group;
- $R^3$ is hydrogen or a linear or branched alkyl radical containing 1–4 carbon atoms in which one or more hydrogen atoms may also be substituted by groups such as alkoxy or fluorine;
- $R^4$ is a hydrogen atom or a linear or branched alkyl radical containing 1–4 carbon atoms in which one hydrogen atom may also be replaced by a group such as alkoxy, carbalkoxy, dialkylamino, 1-aryl or 1-heteroarylpiperazinyl or may be replaced by an aryl or monocyclic 5 or 6 membered heterocycle with one or more heteroatoms N,O,S, such as 1-piperidinyl, 4-morpholinyl, pyridyl, pyrazinyl, pyrimidyl, furyl, imidazolyl, imidazolinyl, thienyl, thiazolyl, 1,2,3- or 1,2,4-triazolyl, optionally mono- or disubstituted with groups such as alkyl, alkoxy, halogen, amino, acylamino, alkylamino, dialkylamino, carbalkoxy, hydroxy, nitrile, nitro and $SO_n$-alkyl, n=0,1 or 2, trifluoromethyl; or $R_4$ is alkenyl or cyclo($C_3$-$C_6$)alkyl and their enantiomers, racemates, diastereoisomers and isomers (E) and (Z), and their salts with pharmaceutically acceptable acids.

The invention also covers a process for the preparation of the hydroxyimino and alkoxyimino compounds of formula I which consists of reacting a 3-acyl-1,4-dihydropyridine with an hydroxylamine of formula $H_2N-O-R^4$ in which $R^4$ has the meaning defined hereinabove, identifying the resulting stereoisomers (E) and (Z) in the mixture and isolating at least one of the two substances in the pure state.

The O-substituted hydroxylamine compounds for formula $H_2N-O-R^4$ used as a starting material may be prepared by methods known in the art, in particular hydrazinolysis of the corresponding $R^4-O-N$-phthalimides followed by acid treatment under mild conditions according to the reaction scheme hereinbelow:

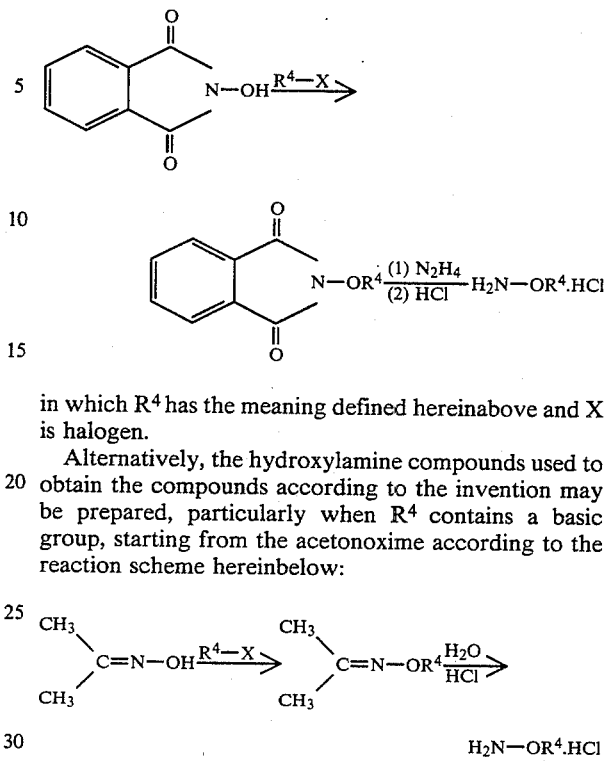

in which $R^4$ has the meaning defined hereinabove and X is halogen.

Alternatively, the hydroxylamine compounds used to obtain the compounds according to the invention may be prepared, particularly when $R^4$ contains a basic group, starting from the acetonoxime according to the reaction scheme hereinbelow:

in which $R^4$ and X have the meaning defined hereinabove.

The following examples are offered only by way of illustration of the present invention.

The melting points have been determined in capillary tubes with a Büchi apparatus and have not been corrected. The ultraviolet spectra have been determined with a Varian CARY 210 apparatus. The pmr spectra have been determined with a VARIAN 60 MHz apparatus in the indicated solvents and using TMS as internal standard.

EXAMPLE 1

Methyl 2,6-dimethyl-3-(1-hydroxyimino)ethyl-4-(3-nitrophenyl)-1,4-dihydropyridine-5-carboxylate (code No. 0227A)

A mixture of 20 g (0.0605 moles) of methyl 2,6-dimethyl-3-acetyl-4-(3-nitrophenyl)-1,4-dihydropyridine-5-carboxylate prepared according to H. Meyer et al, Arzneim. Forsch. 31 (I), 407 (1981), 10 g of pyridine (0.126 moles) and 8.82 g of in hydroxylamine hydrochloride 200 ml of dimethylsulfoxide is allowed to stand at room temperature for about 18 days.

The solution is then poured into water, extracted with methylene chloride, the organic solution is washed with water, dried and concentrated to a small volume affording a precipitate of 3 g of the almost pure hydroxyimino derivative. After recrystallization from dichloroethane, the pure product melts at 194°–195° C.

UV: λmax 337 nm (ε=7.380);

pmr (DMSO-$d_6$): δ1.83 (s, 3H, =C—$CH_3$), 2.00 (s, 3H, =C—$CH_3$), 2.30 (s, 3H, =C—$CH_3$), 3.57 (s, 3H, $OCH_3$), 4.83 (s, 1H, $C_4H$), 7.43–7.73 (m, 2H, =CH ar), 7.83–8.13 (m, 2H, =CH ar), 8.53 (s, 1H, NH), 10.62 (s, 1H, OH).

Elementary analysis:
Calculated for $C_{17}H_{19}N_3O_5$ (345.32): % C=59.12; H=5.55; N=12.16; Found % C=58.92; H=5.64; N=12.03.

EXAMPLE 2

Methyl 2,6-dimethyl-3-(1-methoxyimino)ethyl-4-(3-nitrophenyl)-1,4-dihydropyridin-5-carboxylate (Code No. 0221A)

A mixture of 22.8 g of methyl 2,6-dimethyl-3-acetyl-4-(3-nitrophenyl)-1,4-dihydropyridin-5-carboxylate (0.069 mole), 11.91 g of pyridine and 8.08 g (0.097 moles) of O-methyl-hydroxylamine hydrochloride in 280 ml of methanol is refluxed for 15 hours. The reaction mixture is evaporated to dryness, the oily residue is dissolved in 30 ml of isopropyl alcohol and allowed to stand one hour at −5° C. The small amount of the unreacted 3-acetyl derivative is filtered off, the mixture is evaporated to dryness, dissolved in methylene chloride, washed with water, dried, concentrated and purified by column chromatography on silica gel, eluting with methylene chloride. The fractions containing the two stereoisomers are separately combined. The stereoisomer which is formed in greater amount in the reaction, after recrystallization from cyclohexane, has melting point 128°–130° C.:

UV: λmax 339 nm ($\epsilon$=6.880);

pmr (DMSO-d$_6$): δ1.83 (s, 3H, =C—CH$_3$), 2.00 (s, 3H, =C—CH$_3$), 2.33 (s, 3H, =C—CH$_3$), 3.57 (s, 3H, OCH$_3$), 3.73 (s, 3H, N—OCH$_3$), 4.83 (s, 1H, C$_4$H), 7.40–7.77 (m, 2H, =CH ar), 7.80–8.17 (m, 2H, =CH ar), 8.63 (s, 1H, NH).

Elementary analysis:
Calculated for $C_{18}H_{21}N_3O_5$ (359.38): % C=60.16; H=5.89; N=11.69; Found % C=60.01; H=5.98; N=11.56.

The other stereoisomer has not been isolated in pure form but characterized only in mixtures with the first isomer. In its pmr spectrum, both the protons of a methyl group on double bond and the other values reported hereinbelow are shifted upfield:

pmr (DMSO-d$_6$): δ1.70 (s, 3H, =C—CH$_3$), 4.70 (s, 1H, C$_4$H), 8.50 (s, 1H, NH).

Elementary analysis:
Calculated for $C_{18}H_{21}N_3O_5$ (359.38): % C=60.16; H=5.89; N=11.69; Found % C=60.22; H=6.01; N=11.50.

EXAMPLE 3

(a) N-Ethoxy-phthalimide

A solution of 24 g (0.147 moles) of N-hydroxyphthalimide in 120 ml of dimethyl sulfoxide is warmed at 40° up to complete dissolution. Then 23.9 g (0.176 moles) of sodium acetate trihydrate and 15.92 ml (0.21 moles) of ethyl bromide are added, while warming at 80° C. After two hours and 15 minutes, the mixture is diluted with 600 ml of chloroform, washed with 10% potassium bicarbonate and dried. Removal of the solvent leaves 19.3 g (68.7%) of N-ethoxy-phthalimide, melting point 95°–97° C. (A. Rougny et al, Bull. Soc. Chim. Fr. 1976, pp. 833).

(b) O-Ethyl-hydroxylamine hydrochloride

To a warm solution of 13.7 (71.7 mmoles) of the product prepared in part (a) in 65 ml of ethanol 3.59 g (71.7 mmoles) of hydrazine hydrate are added. The mixture is heated for 20 minutes and then 8.87 ml of 37% HCl are added heating again for 20 minutes. Then 25.3 ml of water are added and the mixture is heated for additional 20 minutes, cooled to 0°, filtered and washed with absolute ethanol. The mother liquors are dried, the residue is dissolved in 100 ml of ethanol, the insoluble product is filtered and the mother liquor dried. The solid thus obtained is washed with boiling ethyl acetate and filtered to give 6 g (86%) of O-ethyl hydroxylamine hydrochloride, melting point 120°–125° (lit. 125°–127° according to B. J. R. Nicolaus et al., *Ann. Chim.* 53, 281 (1963)).

(c) Methyl 2,6-dimethyl-3-(1-ethoxyimino)ethyl-4-(3-nitrophenyl)-1,4-dihydropyridin-5-carboxylate (Code No. 0235A)

Carrying out the process in the same way as in Example 2, but by using O-ethyl-hydroxylamine hydrochloride, after recrystallization from cyclohexane, the product is obtained melting at 123°–125° C., which is analyzed by HPLC and pmr. The product is, to a great extent (>95%), constituted by one of the two stereoisomers:

UV: λmax 339 nm ($\epsilon$=7.377);

pmr (DMSO-d$_6$): δ1.10 (t, 3H, =C—CH$_3$), 1.85 (s, 3H, =C—CH$_3$), 2.00 (s, 3H, =C—CH$_3$), 2.33 (s, 3H, =C—CH$_3$), 3.57 (s, 3H, OCH$_3$), 3.97 (q, 2H, OCH$_2$), 4.80 (s, 1H, C$_4$H), 7.43–7.73 (m, 2H, =CH ar), 7.83–8.17 (m, 2H, =CH ar), 8.57 (s, 1H, NH).

Elementary analysis:
Calculated for $C_{19}H_{23}N_3O_5$ (373.36): % C=61.12; H=6.21; N=11.25; Found: % C=60.94; H=6.34; N=10.90.

The other stereoisomer is identified by the following signals in pmr spectrum:

δ1.70 (s, 3H, =C—CH$_3$), 3.43 (s, 3H, OCH$_3$), 4.70 (s, 1H, C$_4$H), 8.43 (s, 1H, NH).

EXAMPLE 4

Methyl 2,6-dimethyl-3-[1-(ethoxycarbonyl)methoxyimino]ethyl-4-(3-nitrophenyl)-1,4-dihydro-pyridin-5-carboxylate (Code No. 0234A)

Carrying out the reaction in the same manner as in Example 2, but with ethyl aminooxyacetate, a pale yellow oil is obtained. HPLC analysis shows a single peak with an area 97.3%.

By pmr analysis, the following values are obtained:

pmr (DMSO-d$_6$): δ1.20 (t, 3H, CH$_3$), 1.93 (s, 3H, =C—CH$_3$), 2.00 (s, 3H, =C—CH$_3$), 2.30 (s, 3H, =C—CH$_3$), 3.56 (s, 3H, OCH$_3$), 4.10 (q, 2H, OCH$_2$), 4.53 (s, 2H, OCH$_2$CO), 4.77 (s, 1H, C$_4$H), 7.37–7.77 (m, 2H, =CH ar), 7.80–8.17 (m, 2H, =CH ar), 8.63 (s, 1H, NH).

Elementary analysis:
Calculated for $C_{21}H_{25}N_3O_7$ (431.43): % C=58.46; H=5.85; N=9.73 Found: % C=58.64; H=5.96; N=9.52.

The other stereoisomer which cannot be separated by HPLC and which is present in traces is detectable on the basis of the following signals in the pmr spectrum:

δ1.80 (s, 3H, =C—CH$_3$), 3.43 (s, 3H, OCH$_3$), 4.40 (s, 2H, OCH$_2$CO), 4.87 (s, 1H, C$_4$H), 8.43 (s, 1H, NH).

EXAMPLE 5

(a) 2-[2-(N-benzyl-N-methyl-amino)ethoxy]-1,3-isoindolindione

To 100 ml of acetonitrile containing 6.54 g (0.04 mole) of 2-hydroxy-1,3-isoindolindione (N-hydroxyphthalimide), 5.55 ml of triethylamine (0.04 mole), 0.0425 mole of 1-chloro-2-[N-benzyl-N-methylamino]-ethane in 60 ml of benzene (obtained from the hydrochloride by addition of aqueous KOH) are added. The solution is refluxed while the disappearance of the hydroxy-isoindolindione is controlled by the HPLC method. After three hours, the mixture is filtered, concentrated to ⅓ of the initial volume, diluted with 200 ml of methylene chloride and washed with an aqueous solution of potassium bicarbonate. The organic layer is concentrated and the oily residue (8.91 g) is dissolved in boiling cyclohexane. The solution is filtered and concentrated to dryness to afford an oil (8.6 g) which is pure on the basis of HPLC analysis.

pmr (CDCl$_3$): δ2.30 (s, 3H, NCH$_3$), 2.90 (t, 2H, CH$_2$N), 3.63 (s, 2H, ar CH$_2$N), 4.37 (t, 2H, OCH$_2$), 7.30 (s, 5H, =CH ar), 7.65–7.95 (m, 4H, =CH ar).

Elementary analysis:
Calculated for C$_{18}$H$_{18}$N$_2$O$_3$ (310.36): % C=69.66; H=5.85; N=9.02; Found: % C=69.48; H=5.95; N=8.90.

(b) 2-(Aminoxy)-N-benzyl-N-methyl-ethylamine dihydrochloride

The compound prepared in Example 5a), 8.76 g (0.0282 mole) is dissolved in 25 ml of absolute ethanol. The solution is heated to reflux and under efficient stirring, 1.35 g of 100% hydrazine hydrate (0.027 mole) are added. Immediately, a precipitate is formed. After boiling for six minutes, 4.1 ml of concentrated hydrochloric acid are added. After refluxing for an additional 10 minutes, during which the mixture becomes substantially more fluid, 10 ml of water are added. The mixture is allowed to cool in an ice-water bath. The phthalic hydrazide is removed by filtration and the solution is concentrated to dryness. The solid thus obtained is washed several times with boiling ethyl acetate and the supernatant is decanted off. The product, 6.6 g is checked both by perchloric acid as well as iodometric titrations. The results of the pmr analysis in DMSO-d$_6$ are:

δ2.73 (s, 3H, N+CH$_3$), 3.48 (t, 2H, CH$_2$N+), 4.47 (s, 2H, ar CH$_2$N+), 4.67 (t, 2H, OCH$_2$), 7.33–7.83 (m, 5H, =CH ar).

Elementary analysis:
Calculated for C$_{10}$H$_{16}$N$_2$O.2HCl (253,17): % C=47.44; H=7.16; N=11.06; Cl=28.00; Found: % C=47.24; H=7.24; N=10.89; Cl=27.81.

The corresponding base is an oil of pale yellow color: pmr (CDCl$_3$): δ2.27 (s, 3H, NCH$_3$), 2.61 (t, 2H, CH$_2$N), 3.53 (s, 2H, ar CH$_2$N), 3.80 (t, 2H, OCH$_2$), 7.33 (s, 5H, aromatics).

(c) Methyl 2,6-dimethyl-3-[1-(2-N-benzyl-N-methylamino)ethoxy-imino]ethyl-4-(3-nitrophenyl)-1,4-dihydropyridin-5-carboxylate (Code No. 0224A)

Carrying out the process according to Example 2 with methyl 2,6-dimethyl-3-(acetyl-4-(3-nitrophenyl)-1,4-dihydropyridin-5-carboxylate (0.0125 mole), 2-(aminoxy)-N-phenyl-methyl-N-methyl-ethylamine dihydrochloride (0.0125 Mole), and pyridine (0.375 mole) a pale yellow oil is obtained. This is dissolved in isopropyl ether and after a short time, a crystalline product separates which melts at 127°–129° C. The product is analyzed by HPLC and pmr and consists essentially (>90%), of one of the two stereoisomers.

UV: λ246 nm (ε=16.255), λ341 nm (ε=7.155)

pmr (DMSO-d$_6$) δ1.85 (s, 3H, =C—CH$_3$), 1.97 (s, 3H, =C—CH$_3$), 2.13 (s, 3H, NCH$_3$), 2.30 (s, 3H, =C—CH$_3$), 2.50 (t, 2H, CH$_2$N), 3.45 (s, 2H, NCH$_2$ ar), 3.55 (s, 3H, OCH$_3$), 4.07 (t, 2H, OCH$_2$), 4.80 (s, 1H, C$_4$H), 7.30 (s, 5H, =CH ar), 7.40–7.73 (m, 2H, =CH ar), 7.80–8.13 (m, 2H, =CH ar), 8.60 (s, 1H, NH).

The other isomer is identified by the following pmr signals: δ1.68 (s, 3H, =C—CH$_3$), 4.70 (s, 1H, C$_4$H), 8.47 (s, 1H, NH).

Elementary analysis

Calculated for C$_{27}$H$_{32}$N$_4$O$_5$ (492,58): % C=65.84; H=6.55; N=11.37; Found: % C=65.88; H=6.48; N=11.14.

By following essentially the same procedure described in the previous example, the O-substituted hydroxylamines listed in Table I have been prepared. Alternatively, these hydroxylamine compounds may be obtained in a manner analogous to the method described hereinbelow for O-(2-N,N-dimethylamino)ethylhydroxylamine:

A mixture of 7.31 g (0.1 mole) of acetonoxime, 15.844 g (0.11 mole) of 2-N,N-dimethylaminoethylchloride hydrochloride, 41.46 g (0.3 mole) of potassium carbonate and 150 ml of toluene is heated under reflux for 20 hours. After cooling, the solid product is filtered and the mother liquor is concentrated to give 10.77 g of 2-N,N-dimethylaminoethylacetonoxime as an oil. The oil is reacted with 85 ml of 10% hydrochloric acid and the mixture is warmed under reflux for 22 hours. The reaction mixture is concentrated, the residue dissolved in warm ethanol and diethyl ether is added until turbidity. The mixture is cooled and filtered giving 2-(N,N-dimethyl)ethoxyamine, dihydrochloride, 4 g (31%), m.p. 178°–182° C. (R. C. Peterson, Journ. Pharm. Sci. 58, 141 (1969): m.p. 180°–182° C.).

By using a method analogous to the method illustrated in the preceding examples, other products of formula I are prepared which, together with the examples described hereinabove, are listed in Table II.

Other compounds within the scope of the present invention which may be obtained according to the synthetic reaction schemes discussed hereinabove may be prepared using the appropriate intermediates. They are:

ethyl 2,6-dimethyl-3-(1-ethoxyimino)ethyl-4-(2-nitrophenyl)-1,4-dihydropyridin-5-carboxylate;

ethyl 2,6-dimethyl-3-(1-methoxyimino)ethyl-4-(4-nitrophenyl)-1,4-dihydropyridin-5-carboxylate;

(2-methoxy)ethyl 2,6-dimethyl-3-[1-(ethoxycarbonyl)methoxyimino]ethyl-4-(4-nitrophenyl)-1,4-dihydropyridin-5-carboxylate;

isobutyl 2,6-dimethyl-3-(1-cyclopentyloxyimino)ethyl-4-(2-nitrophenyl)-1,4-dihydropyridin-5-carboxylate;

ethyl 2,6-dimethyl-3-(1-isopropyloxyimino)ethyl-4-(2-nitrophenyl)-1,4-dihydropyridin-5-carboxylate;

ethyl 2,6-dimethyl-3-(1-isopropyloxyimino)ethyl-4-(4-nitrophenyl)-1,4-dihydropyridin-5-carboxylate;

methyl 2,6-dimethyl-3-(1-allyloxyimino)ethyl-4-(2-nitrophenyl)-1,4-dihydropyridin-5-carboxylate;

ethyl 2,6-dimethyl-3-(1-benzyloxyimino)ethyl-4-(4-nitrophenyl)-1,4-dihydropyridin-5-carboxylate.

TABLE I

| | R$^4$O—NH$_2$.nHCl | | |
|---|---|---|---|
| R$^4$ | m.p. °C. | yield (%) | Formula |
| CH$_3$ | 148° (dec) | — | CH$_6$ClNO |
| C$_2$H$_5$ | 120–5° | 86 | C$_2$H$_8$ClNO |
| CH(CH$_3$)$_2$ | 80–90° | 77 | C$_3$H$_{10}$ClNO |
| CH$_2$(CH$_2$)$_2$CH$_3$ | 150–2° | 52 | C$_4$H$_{12}$ClNO |
| CH$_2$CH$_2$OC$_2$H$_5$ | oil | 65 | C$_4$H$_{12}$ClNO$_2$ |
| CH$_2$CH=CH$_2$ | 173–7° | — | C$_3$H$_8$ClNO |
| CH$_2$C$_6$H$_5$ | 238° (subl.) | — | C$_7$H$_{10}$ClNO |

TABLE I-continued $R^4O-NH_2 \cdot nHCl$

| $R^4$ | m.p. °C. | yield (%) | Formula |
|---|---|---|---|
| CH(CH₂)₄ (cyclopentyl) | 160–5° | 91 | $C_5H_{12}ClNO$ |
| $CH_2COOC_2H_5$ | 108° | 63 | $C_4H_{10}ClNO_3$ |
| $CH_2CH_2N(CH_3)CH_2C_6H_5$ | 180–5° | 88 | $C_{10}H_{18}Cl_2N_2O$ |
| $CH_2CH_2N(CH_3)_2$ | 178–182° | 23 | $C_4H_{14}Cl_2N_2O$ |
| $CH_2CH_2N$(CH₂)₅ | 197–202° | 24 | $C_7H_{18}Cl_2N_2O$ |

The compounds of the present invention have been evaluated in a series of toxicological-pharmacological tests, the methods and the results of which are summarized hereinbelow:

INTRAVENOUS TOXICITY IN MICE

Male CD1 mice from Charles River, weighing 25 g, are used. Compounds are administered intravenously (i.v.), dissolved in dimethylsulfoxide, and the volume of administration is 0.01 ml/10 g of body weight. The lethal dose, $LD_{50}$ after seven days, is calculated according to the method of Litchfield and Wilcoxon (Exp. Ther. 96, 99 (1949)).

ANTAGONISTIC ACTIVITY TO CALCIUM IN THE TAENIA COLI OF GUINEA PIGS

Hartley albino guinea pigs of average weight 450 g are used. The calcium antagonistic effect is evaluated stimulating the taenia coli, which has been previously depolarized (Naunyn.Schmied. Arch. Pharmacol. 318, 234 (1982)) with a single submaximal concentration of $CaCl_2$ ($10^{-3}M$) at 20 minute intervals. The compounds are allowed to stand in contact with the preparation for ten minutes. The activities $ED_{50}$ are calculated from the maximum percentage of inhibition.

Results:

As it is shown in Table III, the compounds according to the invention exhibit a good calcium antagonistic activity and are therefore useful in the treatment and in the prevention of hypertension, of various forms of angina, of ischemia and of other cardiovascular pathologies.

Some compounds (0265B, 0246B, 0247B, 0270B, 0224A), produce inhibition of contractions due to $CaCl_2$ which increases progressively in spite of repeated washing of the tissue. Due to this phenomenon of inhibition after washing the tissue, the determination of the activity $ED_{50}$ is made taking into consideration the maximum inhibition which is achieved independently from the time of appearance. The data which are available indicate, in addition, that there is a therapeutic index favourable in comparison to the standards, taking into account the marked activity and the toxicity of the compounds of the invention which is, on an average, lower.

TABLE II

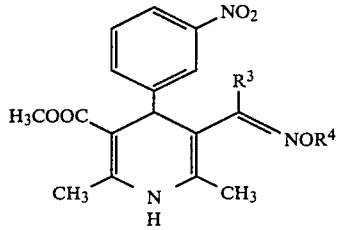

II

| | | | | | Microanalysis | | |
|---|---|---|---|---|---|---|---|
| | | | | | C | H | N |
| Code No. | $R^3$ | $R^4$ | m.p. | Formula | Calcd. & Found | Calcd. & Found | Calcd. & Found |
| 0227A | $CH_3$ | H | 194–195° | $C_{17}H_{19}N_3O_5$ | 59.12–59.06 | 5.54–5.64 | 12.17–12.25 |
| 0221A | $CH_3$ | $CH_3$ | 124–127° | $C_{18}H_{21}N_3O_5$ | 60.16–60.21 | 5.89–5.99 | 11.69–11.80 |
| 0235A | $CH_3$ | $C_2H_5$ | 123–125° | $C_{19}H_{23}N_3O_5$ | 61.11–61.07 | 6.21–6.18 | 11.25–11.30 |
| 0265B | $CH_3$ | $CH(CH_3)_2$ | 122–124° | $C_{20}H_{25}N_3O_5$ | 62.00–61.61 | 6.50–6.48 | 10.84–10.58 |
| 0246B | $CH_3$ | $CH_2(CH_2)_2CH_3$ | 123–124° | $C_{21}H_{27}N_3O_5$ | 62.83–62.91 | 6.78–6.89 | 10.47–10.51 |
| 0254B | $CH_3$ | $CH_2CH_2OC_2H_5$ | 75° | $C_{21}H_{27}N_3O_6$ | 60.42–60.27 | 6.52–6.42 | 10.06–9.94 |
| 0245B | $CH_3$ | $CH_2CH=CH_2$ | 124° | $C_{20}H_{23}N_3O_5$ | 62.33–62.37 | 6.01–6.12 | 10.90–11.01 |
| 0247B | $CH_3$ | $CH_2C_6H_5$ | 144–145° | $C_{24}H_{25}N_3O_5$ | 66.19–65.97 | 5.79–5.83 | 9.65–9.57 |
| 0270B | $CH_3$ | CH(CH₂)₄ | 132–134° | $C_{22}H_{27}N_3O_5$ | 63.91–64.00 | 6.58–6.51 | 10.16–10.01 |
| 0234A | $CH_3$ | $CH_2COOC_2H_5$ | oil | $C_{21}H_{25}N_3O_7$ | 58.46–58.52 | 5.84–5.73 | 9.74–9.88 |
| 0224A | $CH_3$ | $CH_2CH_2N(CH_3)CH_2C_6H_5$ | 127–129° | $C_{27}H_{32}N_4O_5$ | 65.84–65.94 | 6.55–6.64 | 11.37–11.25 |
| 0274B | $CH_3$ | $CH_2CH_2N(CH_3)_2$ | 50–60° | $C_{21}H_{28}N_4O_5$ | 60.56–60.49 | 6.78–6.80 | 13.45–13.51 |
| 0276B | $CH_3$ | $CH_2CH_2N$(CH₂)₅ | 50–60° | $C_{24}H_{32}N_4O_5$ | 61.92–62.01 | 6.93–6.99 | 12.03–11.92 |
| 0286C | $CH_2OCH_3$ | $CH_2CH_2OC_2H_5$ | oil | $C_{22}H_{29}N_3O_7$ | 59.05–59.38 | 6.53–6.41 | 9.39–9.50 |

TABLE III

Ca—antagonistic activity in vitro (Taenia Coli) and acute toxicity in mice by the intravenous route of the compounds of Formula I

| Code No. | $LD_{50}$ in mice i.v. (mg/kg) | Ca—antagonistic activity in vitro $ED_{50} \times 10^{-9}M$ |
|---|---|---|
| 0227A | 15.2 (10.0–20.9) | 270 |
| 0251A | 27.3 (18.4–40.5) | 26 |
| 0235A | 30.6 (25.7–36.5) | 7.4 |
| 0265B | 27.6 (23.4–32.6) | 4.4 |
| 0246B | 37.5 (28.8–48.8) | 7 |
| 0254B | 35.0 (26.5–46.2) | 5.9 |
| 0245B | 35.4 (30.8–40.7) | 4.7 |
| 0247B | 28.9 (24.3–34.4) | 4.8 |
| 0270B | 70.3 (59.1–83.7) | 5.6 |
| 0234A | 17.3 (12.2–24.5) | 29 |
| 0224A | 3.3 (1.9–5.7) | 18 |
| 0274B | 38.3 (31–47.1) | 510 |

TABLE III-continued

Ca—antagonistic activity in vitro (*Taenia Coli*) and acute toxicity in mice by the intravenous route of the compounds of Formula I

| Code No. | LD$_{50}$ in mice i.v. (mg/kg) | Ca—antagonistic activity in vitro ED$_{50}$ × 10$^{-9}$M |
|---|---|---|
| 0276B | 22.7 (16.1–32.0) | 220 |
| 0286C | >160 | 370 |
| Nifedipine | 10.8 (9.2–12.8) | 2.6 |
| Nicardipine | 17.4 (11.0–27.5) | 2.3 |
| Nitrendipine | 34.5 (32.5–36.5) | 1.9 |

The present invention also covers all the industrial aspects resulting from the therapeutic use of the compounds of Formula I. An essential aspect of the invention also includes the pharmaceutical compositions which contain predetermined amounts of the products according to the present invention and their salts. The compounds according to the invention may be administered by the oral route or the parenteral route, for instance in the form of tablets, capsules, small envelopes, which contain hydrodispersible powders and injection vials. The compounds of the invention can be administered in humans 1–3 times a day at doses of 10–100 mg. The pharmaceutical compositions of the present invention contain in addition to the active component also an inert excipient.

We claim:

1. A compound of formula I:

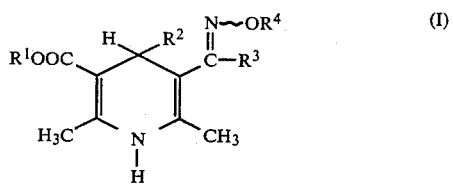

wherein
$R^1$ is a linear or branched alkyl radical containing between 1 and 5 carbon atoms, said alkyl radical being unsubstituted or substituted by an alkoxy group;
$R^2$ is an unsubstituted phenyl or phenyl substituted by a nitro group;
$R^3$ is hydrogen or a linear or branched alkyl residue containing between 1 and 4 carbon atoms, said alkyl radical being unsubstituted or substituted by at least one alkoxy or fluorine atom or both alkoxy and fluorine atoms;
$R^4$ is hydrogen or a linear or branched alkyl containing between 1 and 4 carbon atoms, said alkyl radical being unsubstituted or substituted by alkoxy, carbalkoxy, dialkylamino, monocyclic aryl, or monocyclic heterocyclic ring which is 1-piperidinyl, 4-morpholinyl, pyridyl, pyrazinyl, pyrimidyl, furyl, imidazolyl, imidazolinyl, thienyl, thiazolyl, 1,2,3-triazolyl, 1,2,4-triazolyl, said monocyclic ring being unsubstituted or being mono- or di-substituted with alkyl, alkoxy, halogen, amino, acylamino, alkylamino, dialkylamino, carbalkoxy, hydroxy, nitrile, nitro and SO$_n$-alkyl, wherein n=0.1 or 2, or trifluoromethyl or $R^4$ is alkenyl or cyclo (C$_3$–C$_6$) alkyl and its enantiomers, racemates, diastereoisomers and isomers (E) and (Z) thereof, and their salts with a pharmaceutically acceptable acid.

2. The compound according to claim 1 which is methyl 2,6-(dimethyl-3-(1-hydroxyimino)ethyl-4-(3-nitrophenyl)-1,4-dihydropyridin-5-carboxylate.

3. The compound according to claim 1 which is methyl 2,6-dimethyl-3-(1-methoxyimino)ethyl-4-(3-nitrophenyl)-1,4-dihydropyridin-5-carboxylate.

4. The compound according to claim 1 which is methyl 2,6-dimethyl-3-(1-ethoxyimino)ethyl-4-(3-nitrophenyl)-1,4-dihydropyridin-5-carboxylate.

5. The compound according to claim 1 which is methyl 2,6-dimethyl-3-(1-isopropoxyimino)ethyl-4-(3-nitrophenyl)-1,4-dihydropyridin-5-carboxylate.

6. The compound according to claim 1 which is methyl 2,6-dimethyl-3-(1-n-butyloxyimino)ethyl-4-(3-nitrophenyl)-1,4-dihydropyridin-5-carboxylate.

7. The compound according to claim 1 which is methyl 2,6-dimethyl-3-[1-(2-ethoxy)-ethoxyimino]ethyl-4-(3-nitrophenyl)-1,4-dihydropyridin-5-carboxylate.

8. The compound according to claim 1 which is methyl 2,6-dimethyl-3-(1-allyloxyimino)ethyl-4-(3-nitrophenyl)-1,4-dihydropyridin-5-carboxylate.

9. The compound according to claim 1 which is methyl 2,6-dimethyl-3-(1-benzyloxyimino)ethyl-4-(3-nitrophenyl)-1,4-dihydropyridin-5-carboxylate.

10. The compound according to claim 1 which is methyl 2,6-dimethyl-3-(1-cyclopentyloxyimino)ethyl-4-(3-nitrophenyl)-1,4-dihydropyridin-5-carboxylate.

11. The compound according to claim 1 which is methyl 2,6-dimethyl-3-(1ethoxycarbonyl-methoxyimino)-ethyl-4-(3-nitrophenyl)-1,4-dihydropyridin-5-carboxylate.

12. The compound according to claim 1 which is methyl 2,6-dimethyl-3-[1-(2-N-benzyl-N-methylamino)ethoxyimino]ethyl-4-(3-nitrophenyl)-1,4-dihydropyridin-5-carboxylate.

13. The compound according to claim 1 which is methyl 2,6-dimethyl-3-[(2-N,N-dimethylamino)ethoxyimino]ethyl-4-(3-nitrophenyl)-1,4-dihydropyridin-5-carboxylate.

14. The compound according to claim 1 which is methyl 2,6-dimethyl-3-[1-(2-piperidino)ethoxyimino]ethyl-4-(3-nitrophenyl)-1,4-dihydropyridin-5-carboxylate.

15. The compound according to claim 1 which is methyl 2,6-dimethyl-3-[1-(2-ethoxy)ethoxyimino-2-methoxy]ethyl-4-(3-nitrophenyl)-1,4-dihydropyridin-5-carboxylate.

16. An antihypertensive composition which consists of an amount of a compound of claim 1 effective in the treatment of hypertension, and a pharmaceutically acceptable carrier.

17. The composition according to claim 16 wherein said compound is present in unit dosage form of tablets, capsules, small envelopes, powders, vials.

* * * * *